(12) United States Patent
Zhang et al.

(10) Patent No.: US 11,968,492 B2
(45) Date of Patent: Apr. 23, 2024

(54) EARPHONE

(71) Applicant: Anhui Huami Information Technology Co., Ltd., Anhui FTZ (CN)

(72) Inventors: Yi Zhang, Anhui FTZ (CN); Dong Ao, Anhui FTZ (CN); Qi An, Anhui FTZ (CN)

(73) Assignee: Anhui Huami Information Technology Co., Ltd., Anhui FTZ (CN)

( * ) Notice: Subject to any disclaimer, the term of this patent is extended or adjusted under 35 U.S.C. 154(b) by 153 days.

(21) Appl. No.: 17/748,625

(22) Filed: May 19, 2022

(65) Prior Publication Data
US 2022/0279262 A1    Sep. 1, 2022

Related U.S. Application Data

(63) Continuation of application No. PCT/CN2020/130624, filed on Nov. 20, 2020.

(30) Foreign Application Priority Data

Nov. 20, 2019  (CN) .......................... 201911142545.5
Nov. 20, 2019  (CN) .......................... 201922020668.3

(51) Int. Cl.
  *H04R 1/10*   (2006.01)
  *A61B 5/024*  (2006.01)

(52) U.S. Cl.
  CPC ......... *H04R 1/105* (2013.01); *A61B 5/02438* (2013.01); *H04R 1/1016* (2013.01); *H04R 1/1066* (2013.01); *H04R 1/1091* (2013.01)

(58) Field of Classification Search
  CPC ........ H04R 1/10; H04R 1/1016; H04R 1/105; H04R 1/1066; H04R 1/1091;
  (Continued)

(56) References Cited

U.S. PATENT DOCUMENTS

2017/0134845 A1   5/2017  Milam et al.
2017/0195767 A1*  7/2017  Kim ........................ H04R 5/033
(Continued)

FOREIGN PATENT DOCUMENTS

CN    205491028 U    8/2016
CN    106941638 A    7/2017
(Continued)

OTHER PUBLICATIONS

International Search Report for International Application No. PCT/CN2020/130624 dated Feb. 8, 2021.

*Primary Examiner* — Thang V Tran
(74) *Attorney, Agent, or Firm* — Young Basile Hanlon & MacFarlane, P.C.

(57) ABSTRACT

Described herein is an earphone including an ear hook portion and an earphone portion, the ear hook portion is provided with a first magnetic attraction member, the earphone portion is provided with a second magnetic attraction member, and the second magnetic attraction member attracts and cooperates with the first magnetic attraction member to connect the earphone portion with the ear hook portion; a heart rate detection module, the heart rate detection module is arranged on the ear hook portion and/or earphone portion.

19 Claims, 2 Drawing Sheets

(58) Field of Classification Search
CPC ........ H04R 1/1025; H04R 1/02; H04R 1/028; H04R 25/30; H04R 25/50; H04R 25/55; H04R 25/556; H04R 25/505; H04R 25/507; H04R 25/60; H04R 25/607; H04R 25/65; A61B 5/682; A61B 5/6815; A61B 5/02438
See application file for complete search history.

(56) References Cited

U.S. PATENT DOCUMENTS

| | | | |
|---|---|---|---|
| 2017/0195768 A1* | 7/2017 | Kim | H04R 1/08 |
| 2018/0184191 A1* | 6/2018 | Kim | H04R 1/1041 |
| 2022/0086555 A1* | 3/2022 | Narisawa | H04R 1/105 |

FOREIGN PATENT DOCUMENTS

| | | |
|---|---|---|
| CN | 207283765 U | 4/2018 |
| CN | 210469695 U | 5/2020 |

* cited by examiner

EARPHONE

CROSS-REFERENCE TO RELATED APPLICATION(S)

The present disclosure is a continuation of PCT/CN2020/130624, filed Nov. 20, 2020, which claims priority and benefit of Chinese Patent Application No. 201911142545.5 and Chinese Patent Application No. 201922020668.3, both filed on Nov. 20, 2019, the entire contents of all of which are incorporated herein as reference.

TECHNICAL FIELD

Implementations of the present disclosure relates to a technical field of earphones, and more particularly, to an earphone.

BACKGROUND

In a related art, an earphone and an ear hook are configured as one integrated piece, which is difficult for user to wear, and the ear will feel pain after wearing the ear hook for a long time.

SUMMARY

The present disclosure is based on inventors' findings and knowledge of the following technical problems and facts.

In a related art, an earphone is connected to an ear hook through a snap. However, it is easy to be damaged at the snap, and the snap has a short service life.

To this end, implementations of the present disclosure propose an earphone, which has advantages of low wearing difficulty, high comfort, a long service life and small volume for a charging box.

The earphone according to the implementations of the present disclosure includes an ear hook portion provided with a first magnetic attraction member; an earphone portion provided with a second magnetic attraction member, the second magnetic attraction member attracting and cooperating with the first magnetic attraction member such that the earphone portion is connected with the ear hook portion; and a heart rate detection module arranged on at least one of the ear hook portion or the earphone portion.

In the earphone according to the implementations of the present disclosure, through the arrangement of the first magnetic attraction member and the second magnetic attraction member, the ear hook portion is detachably connected to the earphone portion through the first magnetic attraction member and the second magnetic attraction member. Compared with a connection mode by means of the snap, the cooperation mode by means of magnetic attraction is more convenient for the disassembly and the assembly with less wear during the disassembly and the assembly, and the service life is longer. Moreover, the cooperation mode by means of the magnetic attraction may also reduce the difficulty of wearing and improve the user experience. Secondly, when the user exercises, the ear hook portion may be connected to the earphone portion, so that the wearing can be more reliable to support the user's strenuous exercise When the user does not exercise, he may only wear the earphone portion, so as to reduce the force exerted by the earphone on ears, improve user comfort, while the use is more convenient. Furthermore, when the user charges the earphone, the ear hook portion and the earphone portion may be placed separately in a charging box after disassembled, so as to greatly reduce the volume of the charging box. In addition, the earphone is further provided with the heart rate detection module. The heart rate detection module may detect the heart rate of the user in real time, so that the user may obtain his own health status more accurately and timely.

According to some implementations of the present disclosure, an end of the ear hook portion is defined with a first limit groove, the first magnetic attraction member is arranged in the first limit groove, an end of the earphone portion is defined with a second limit groove, and the second magnetic attraction member is arranged in the second limit groove.

According to some implementations of the present disclosure, at least one of the first magnetic attraction member and the second magnetic attraction member is a magnet.

According to some implementations of the present disclosure, the earphone portion is provided with an earphone chip, the heart rate detection module is electrically connected to the earphone chip, the earphone further includes a connection sensor for detecting a connection state between the ear hook portion and the earphone portion, and the connection sensor is electrically connected to the earphone chip.

According to some implementations of the present disclosure, the first magnetic attraction member is a magnet, the connection sensor is a Hall sensor arranged on the earphone portion, and the Hall sensor is spaced apart from the second magnetic attraction member when the second magnetic attraction member is a magnet.

According to some implementations of the present disclosure, the earphone portion is further provided with a Bluetooth module electrically connected to the earphone chip.

According to some implementations of the present disclosure, the heart rate detection module is arranged on the earphone portion, the earphone portion is provided with a first battery electrically connected to the heart rate detection module.

According to some implementations of the present disclosure, the heart rate detection module is arranged on the ear hook portion, the ear hook portion is provided with a second battery electrically connected to the heart rate detection module.

According to some implementations of the present disclosure, one of the ear hook portion and the earphone portion is provided with an elastic piece, the other one of the ear hook portion and the earphone portion is provided with a contact point, and the heart rate detection module is electrically connected to the earphone chip through a cooperation between the elastic piece and the contact point.

According to some implementations of the present disclosure, one of the ear hook portion and the earphone portion is provided with a pin, the other one of the ear hook portion and the earphone portion is provided with a jack, and the heart rate detection module is electrically connected to the earphone chip through a cooperation between the pin and the jack.

Additional aspects and advantages of the present disclosure will be given in part in the following description, become apparent in part from the following description, or be learned from the practice of the present disclosure.

Figure 1:
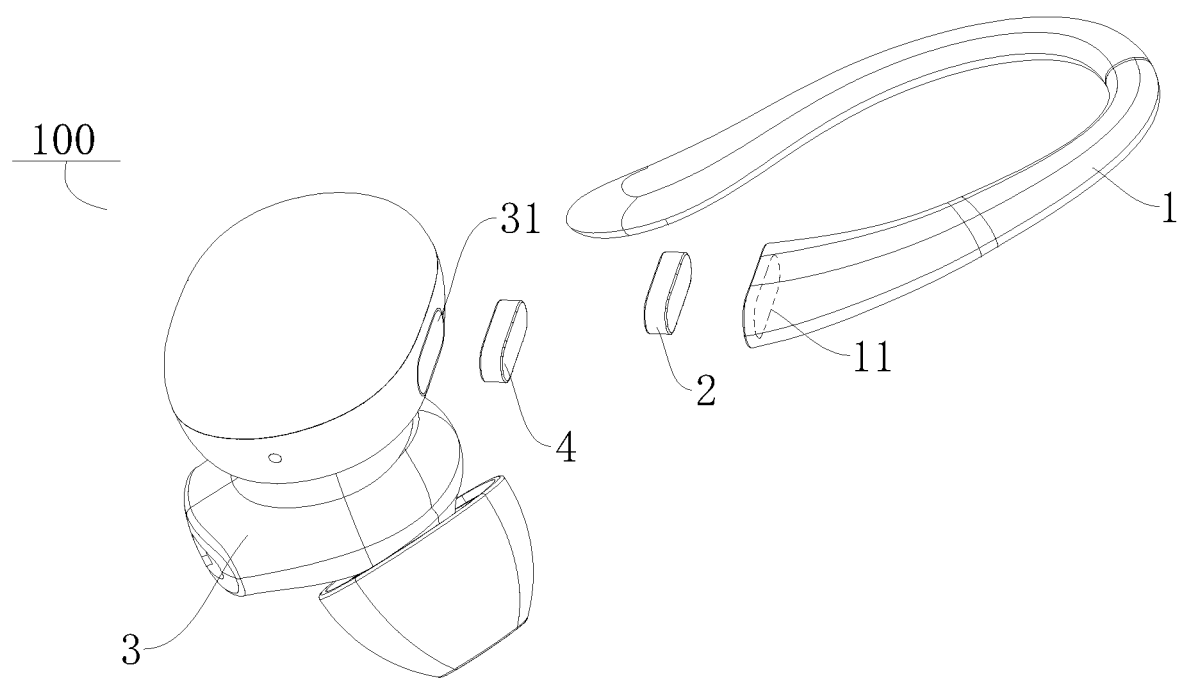
FIG. 1 is an exploded view of an earphone according to an implementation of the present disclosure.

REFERENCE NUMERALS earphone 100,
ear hook portion 1, first limit groove 11,
first magnetic attraction member 2,
earphone portion 3, second limit groove 31,
second magnetic attraction member 4, heart rate detection module 5,
earphone chip 6, connection sensor 7, Bluetooth module 8,
charging box 200.

DETAILED DESCRIPTION

Implementations of the present disclosure are described in detail below, and examples of the described implementations are shown in accompanying drawings. The following implementations described with reference to the accompanying drawings are exemplary and are intended to explain the present disclosure, and cannot be construed as a limitation to the present disclosure. In the description of the present disclosure, it shall be understood that terms such as "central," "longitudinal," "transverse," "length," "width," "thickness," "upper," "lower," "front," "rear," "left," "right," "vertical," "horizontal," "top," "bottom," "inner," "outer," "clockwise," "counterclockwise," "axial," "radial" and "circumferential" indicate the orientation or position relationship based on the orientation or position relationship illustrated in the drawings only for convenience of description or for simplifying description of the present disclosure, and do not indicate or imply that the device or element referred to must have a particular orientation or be constructed and operated in a specific orientation, and hence cannot be construed as limitation to the present disclosure.

Figure 2:
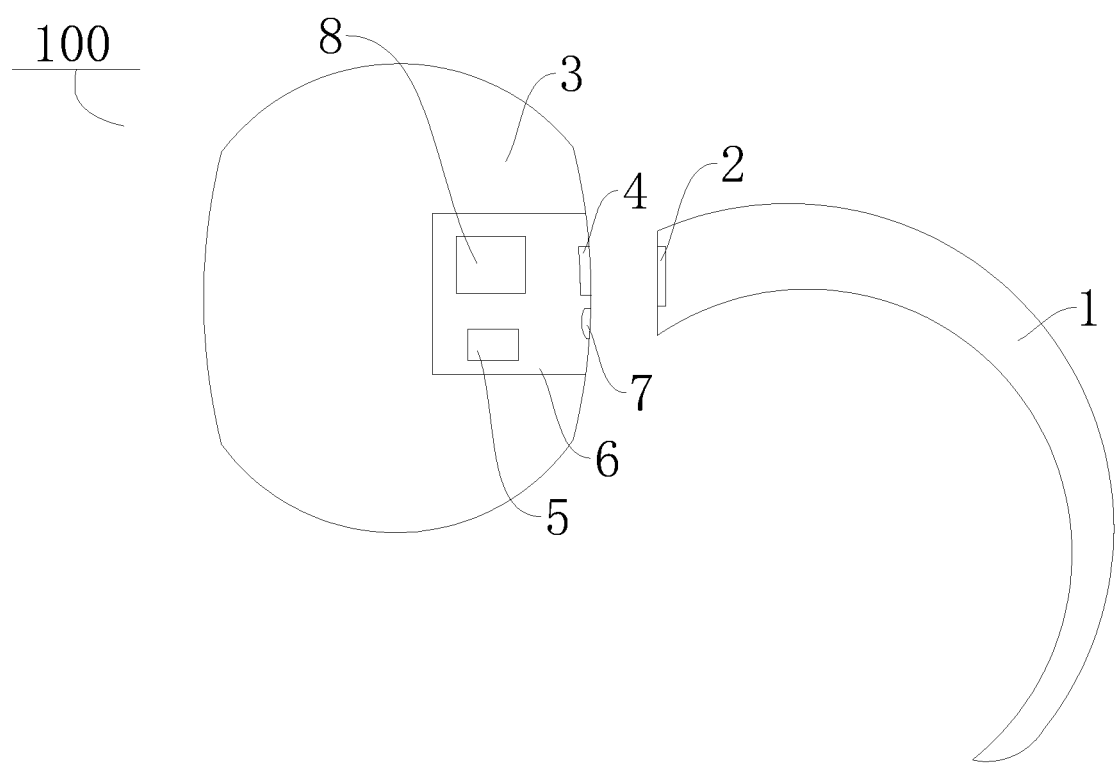
FIG. 2 is a schematic view of an earphone according to an implementation of the present disclosure.

As shown in FIG. 1 and FIG. 2, an earphone 100 according to implementations of the present disclosure includes an ear hook portion 1, an earphone portion 3 and a heart rate detection module 5.

Specifically, as shown in FIG. 1 and FIG. 2, the ear hook portion 1 is provided with a first magnetic attraction member 2, the earphone portion 3 is provided with a second magnetic attraction member 4, and the second magnetic attraction member 4 attracts and cooperates with the first magnetic attraction member 2 such that the earphone portion 3 is connected with the ear hook portion 1. It may be understood that the ear hook portion 1 and the earphone portion 3 may be detachably connected through the first magnetic attraction member 2 and the second magnetic attraction member 4. When the earphone is worn by a user, the ear hook portion 1 may be worn first, and then the earphone portion 3 may be attracted onto the ear hook portion 1. Thus, the difficulty of wearing the earphone 100 may be reduced by wearing the ear hook portion 1 and the earphone portion 3 step by step, and the user experience is improved.

In a related art, the earphone portion and the ear hook portion are connected through a snap connection, which makes it easy to be damaged at the snap and causing short service life. However, in the present disclosure, the earphone portion 3 and the ear hook portion 1 may be connected through the first magnetic attraction member 2 and the second magnetic attraction member 4, which makes the service life relatively long. Moreover, a magnetic attraction connection using the first magnetic attraction member 2 and the second magnetic attraction member 4 is less difficult than the snap connection, and the disassembly and the assembly are more convenient.

Figure 3:
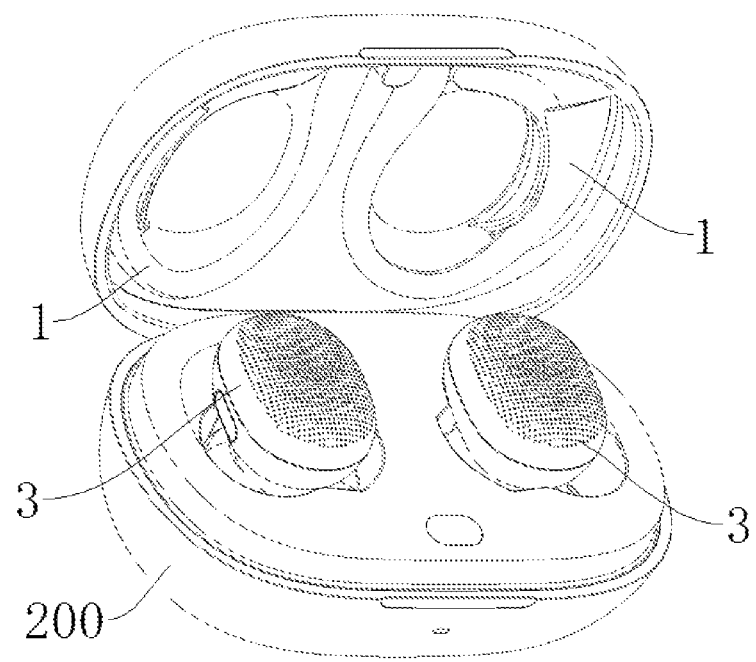
FIG. 3 is a schematic view of an earphone and a charging box according to an implementation of the present disclosure.

Secondly, when the user exercises, the ear hook portion 1 may be connected to the earphone portion 3, so that the wearing can be more reliable to support the user's strenuous exercise. When the user is not exercising, he may only wear the earphone portion 3, so as to reduce a force exerted by the earphone 100 on ears, improve user comfort, while making the use more convenient. Moreover, when the user charges the earphone 100, the ear hook portion 1 and the earphone portion 3 may be placed separately in a charging box 200 after disassembling, so as to greatly reduce volume of the charging box 200. For example, in an implementation shown in FIG. 3, the ear hook portion 1 and the earphone portion 3 may be placed separately in the charging box 200. Compared with an integrated earphone in the related art, the volume of the charging box 200 occupied by the earphone 100 in the present disclosure is smaller, so that a size of the charging box 200 may be reduced, which makes it convenient for the user to carry the charging box.

As shown in FIG. 1 and FIG. 2, as an implementation, a heart rate detection module 5 is arranged on the ear hook portion 1 and/or the earphone portion 3. Preferably, the heart rate detection module 5 is arranged on the ear hook portion 1 or on the earphone portion 3. The heart rate detection module 5 may detect a heart rate of the user in real time. Since the heart rate detection module 5 is arranged on the earphone 100, the user may obtain his own health status more accurately and timely.

It should be noted that in some implementations of the present disclosure, a plurality of first magnetic attraction members 2 may be provided, and a second magnetic attraction member 4 or a plurality of second magnetic attraction members 4 may be provided. Alternatively, a plurality of second magnetic attraction members 4 may be provided, and a first magnetic attraction member 2 or a plurality of first magnetic attraction members 2 may be provided.

In the earphone 100 according to the implementations of the present disclosure, through the arrangement of the first magnetic attraction member 2 and the second magnetic attraction member 4, the ear hook portion 1 and the earphone portion 3 may be detachably connected through the first magnetic attraction member 2 and the second magnetic attraction member 4. Compared with the connection mode by means of the snap, the cooperation mode by means of magnetic attraction is more convenient for the disassembly and the assembly with less wear during the disassembly and the assembly, and the service life is longer. Moreover, the cooperation mode by means of the magnetic attraction may also reduce the difficulty of wearing and thus improve the user experience. Secondly, when the user exercises, the ear hook portion 1 may be connected to the earphone portion 3, so that the wearing can be more reliable to support the user's strenuous exercise, When the user does not exercise, he may only wear the earphone portion 3, so as to reduce the force exerted by the earphone 100 on ears, improve user comfort, while the use is more convenient for the user. Furthermore, when the user charges the earphone 100, the ear hook portion 1 and the earphone portion 3 may be placed separately in a charging box 200 after disassembled, so as to greatly reduce the volume of the charging box 200. In addition, the earphone 100 is further provided with the heart rate detection module 5. The heart rate detection module 5 may detect the heart rate of the user in real time, so that the user may obtain his own health status more accurately and timely.

According to some implementations of the present disclosure, as shown in FIG. 1 and FIG. 2, an end of the ear hook portion 1 is defined with a first limit groove 11, the first magnetic attraction member 2 is arranged in the first limit groove 11, an end of the earphone portion 3 is defined with a second limit groove 31, and the second magnetic attraction member 4 is arranged in the second limit groove 31. The first limit groove 11 has a function of accommodating and limiting the first magnetic attraction member 2. Through the arrangement that the first limit groove 11 is defined in the ear hook portion 1, the first magnetic attraction member 2 may be fixed on the ear hook portion 1, so as to realize the integration of the first magnetic attraction member 2 and the ear hook portion 1. Similarly, the second limit groove 31 also has a function of accommodating and limiting the second magnetic attraction member 4. Through the arrangement that the second limit groove 31 is defined in the earphone portion 3, the second magnetic attraction member 4 may be fixed on the earphone portion 3, so as to realize the integration of the second magnetic attraction member 4 and the earphone portion 3. Specifically, in an example of the present disclosure, the first magnetic attraction member 2 is in an interference fit with the first limit groove 11, and the second magnetic attraction member 4 is in an interference fit with the second limit groove 31.

According to some implementations of the present disclosure, at least one of the first magnetic attraction member 2 and the second magnetic attraction member 4 is a magnet. In some implementations, only the first magnetic attraction member 2 may be a magnet; or, in some implementations, only the second magnetic attraction member 4 is a magnet; or, in some implementations, both the first magnetic attraction member 2 and the second magnetic attraction member 4 are a magnet. For example, in an example of the present disclosure, the first magnetic attraction member 2 is a magnet and the second magnetic attraction member 4 is an iron piece, so that a connection between the ear hook portion 1 and the earphone portion 3 is realized by using the principle that the magnet and the iron attract each other. For another example, in another example implementation of the present disclosure, the first magnetic attraction member 2 is an iron piece and the second magnetic attraction member 4 is a magnet. For yet another example, in another example implementation of the present disclosure, the first magnetic attraction member 2 is a magnet, the second magnetic attraction member 4 is a magnet, and a magnetism of the first magnetic attraction member 2 is opposite to a magnetism of the second magnetic attraction member 4. It should be noted that the above magnet may be a permanent magnet or an electromagnet.

According to some implementations of the present disclosure, as shown in FIG. 1 and FIG. 2, the earphone portion 3 is provided with an earphone chip 6, the heart rate detection module 5 is electrically connected to the earphone chip 6, the earphone 100 further includes a connection sensor 7 for detecting a connection state between the ear hook portion 1 and the earphone portion 3, and the connection sensor 7 is electrically connected to the earphone chip 6. The connection sensor 7 may be a Hall sensor, a pressure sensor, a photoelectric sensor, etc. In an implementation, the connection sensor 7 is preferably selected as the Hall sensor. When the earphone portion 3 is connected to the ear hook portion 1, the connection sensor 7 sends a signal showing that the ear hook portion 1 is connected to the earphone portion 3, which indicates that the user is about to enter a sport mode, and the earphone chip 6 receives the signal sent by the connection sensor 7, controls the heart rate detection module 5 to operate, detects data of the heart rate of the user in real time, and switches play mode of the earphone into a sport style.

It may be understood that the sport style may be a preset equalizer mode (such as a rock mode or a user-defined mode), or the sport style may be set to play a preset track with a strong rhythm, etc. When the ear hook portion 1 is disconnected from the earphone portion 3, which indicates that that the user ends the sport, the connection sensor 7 detects the disconnection. Meanwhile, the earphone chip 6 controls the heart rate detection module 5 to stop collecting the data of the heart rate and switches the play mode back into a normal style.

In some implementations of the present disclosure, the first magnetic attraction member 2 is the magnet, the connection sensor 7 is the Hall sensor arranged on the earphone portion 3. It may be understood that when the earphone portion 3 is connected to the ear hook portion 1, the connection sensor 7 may sense a magnetic field of the first magnetic attraction member 2, and meanwhile the connection sensor 7 may send a signal to the earphone chip 6, and after receiving the signal from the connection sensor 7, the earphone chip 6 may control the heart rate detection module 5 to operate.

In the related art, the earphone portion is provided with a button, and the user may turn on the heart rate detection module by pressing the button. However, according to implementations provided in the present disclosure, when the earphone portion 3 is connected to the ear hook portion 1, which indicates that the user is about to enter the sport mode, the heart rate detection module 5 may be automatically turned on; when the ear hook portion 1 is disconnected from the earphone portion 3, which indicates that the user ends the sport, the heart rate detection module 5 may be automatically turned off, so that it is no longer necessary to turn on/off the heart rate detection module 5 manually. Thus, according to implementations of this disclosure, it is more convenient for the user to use the earphone, as the heart rate detection module 5 can be turned off in time, which improves the endurance of the earphone 100. On the other hand, a music playing mode may be switched automatically, thus improving the user experience. Furthermore, according implementations of this disclosure, the button typically provided with earphone may be removed from the design, so that the size of the earphone portion 3 may be reduced, which is conducive to miniaturization of the earphone portion 3, as well as facilitating waterproof performance as well as dustproof performance of the earphone 100.

In some implementations of the present disclosure, as shown in FIG. 1 and FIG. 2, the Hall sensor is arranged on the earphone portion 3 and spaced apart from the second magnetic attraction member 4 when the second magnetic attraction member 4 is a magnet. It may be understood that when the second magnetic attraction member 4 is the magnet, the second magnetic attraction member 4 has a certain magnetic field strength. By separating the Hall sensor from the second magnetic attraction member 4, the magnetic field of the second magnetic attraction member 4 may be avoided from interfering with the magnetic field of the first magnetic attraction member 2 sensed by the hall sensor. Therefore, the sensing accuracy of the Hall sensor may be improved.

In some implementations of the present disclosure, as shown in FIG. 1 and FIG. 2, the earphone portion 3 is further provided with a Bluetooth module 8 electrically connected to the earphone chip 6. It may be understood that the heart rate detection module 5 may transmit the detected heart rate information to the earphone chip 6, then the earphone chip 6 transmits the obtained heart rate information to the Bluetooth module 8, and afterwards, the Bluetooth module 8 transmits the heart rate information to a mobile terminal connected to the Bluetooth module 8 over the Bluetooth. The user may know his own heart rate information through the mobile terminal.

In some implementations of the present disclosure, as shown in FIG. 1 and FIG. 2, the heart rate detection module 5 is arranged on the earphone portion 3, the earphone portion 3 is provided with a first battery electrically connected to the heart rate detection module 5. It may be understood that the earphone portion 3 is provided with the first battery, and the first battery may supply power to the heart rate detection module 5. It should be noted that the first battery on the earphone portion 3 may also supply power to other modules on the earphone portion 3.

For example, in an example implementation of the present disclosure, the heart rate detection module 5 is arranged on the earphone portion 3. When the user connects the earphone portion 3 with the ear hook portion 1, the connection sensor 7 on the earphone portion 3 may sense the first magnetic attraction member 2 on the ear hook portion 1, and then transmit a signal to the earphone chip 6. When receiving the signal sent by the connection sensor 7, the earphone chip 6 may control the heart rate detection module 5 to turn on.

It should be noted that the earphone 100 may be connected to the mobile terminal via the Bluetooth module 8 over the Bluetooth. When receiving the signal sent by the connection sensor 7 indicating that the earphone portion 3 is connected to the ear hook portion 1, the earphone chip 6 may transmit information to the mobile terminal, and display a reminder whether to turn on the sport mode on the mobile terminal. When the user selects to enter the sport mode, the play mode of the earphone 100 automatically enters the sport style. Of course, the present disclosure is not limited to this. When receiving the signal sent by the connection sensor 7, the earphone chip 6 may also directly control the play mode of the earphone 100 to be switched into the sport mode. When receiving the signal sent by the connection sensor 7 indicating that the earphone portion 3 is disconnected from the ear hook portion 1, the earphone chip 6 may control the heart rate detection module 5 to turn off and switch the sport mode of the earphone 100 into the normal play mode, so that the endurance ability of the earphone 100 and the user experience are improved.

In some implementations of the present disclosure, the heart rate detection module 5 is arranged on the ear hook portion 1, the ear hook portion 1 is provided with a second battery electrically connected to the heart rate detection module 5. By arranging the heart rate detection module 5 on the ear hook portion 1, a space of the earphone portion 3 occupied by the heart rate detection module 5 may be reduced, so as to realize the miniaturization of the earphone portion 3, such that the earphone portion 3 is more aesthetic and concise.

For example, in an example implementation of the present disclosure, the heart rate detection module 5 is arranged on the ear hook portion 1. When the user connects the earphone portion 3 with the ear hook portion 1, the Hall sensor on the earphone portion 3 may sense the magnet on the ear hook portion 1, and then transmit a signal to the earphone chip 6. When receiving the signal sent by the Hall sensor, the earphone chip 6 controls the heart rate detection module 5 to turn on.

In some implementations of the present disclosure, the heart rate detection module 5 is arranged on the ear hook portion 1, one of the ear hook portion 1 and the earphone portion 3 is provided with an elastic piece, the other one of the ear hook portion 1 and the earphone portion 3 is provided with a contact point, and through a cooperation between the elastic piece and the contact point, the heart rate detection module 5 is electrically connected to the earphone chip 6. It may be understood that, compared to the connection using the connecting wires, the cooperation and connection between the elastic piece and the contact point may reduce the difficulty of the electrical connection between the heart rate detection module 5 and the earphone chip 6, which improves the efficiency of the electrical connection between the heart rate detection module 5 and the earphone chip 6, and ensures the stability of the electrical connection between the heart rate detection module 5 and the earphone chip 6.

For example, in an example implementation of the present disclosure, the heart rate detection module 5 may transmit the detected data information to the earphone chip 6 through the cooperation between the elastic piece and the contact point, and the earphone chip 6 transmits the obtained data information to the external mobile terminal through the Bluetooth module 8.

In other implementations of the present disclosure, one of the ear hook portion 1 and the earphone portion 3 is provided with a pin, and the other one of the ear hook portion 1 and the earphone portion 3 is provided with a jack. The heart rate detection module 5 is electrically connected to the earphone chip 6 through a cooperation of the pin and the jack. Through the cooperation of pin and jack, the difficulty of electrical connection between heart rate detection module 5 and earphone chip 6 may be reduced, the efficiency of the electrical connection between heart rate detection module 5 and earphone chip 6 may be improved, and the stability of the electrical connection between heart rate detection module 5 and earphone chip 6 may be guaranteed.

In the description of this specification, terms such as "an implementation," "some implementations," "an example," "a specific example," or "some examples," means that a particular feature, structure, material, or characteristic described in connection with the implementation or example is included in at least one implementation or example of the present disclosure. Thus, the appearances of these terms in various places throughout this specification are not necessarily referring to the same implementation or example of the present disclosure. Furthermore, the particular features, structures, materials, or characteristics may be combined in any suitable manner in one or more implementations or examples. In addition, without contradiction, those skilled in the art may combine and unite different implementations or examples or features of the different implementations or examples described in this specification.

In the present disclosure, unless otherwise explicitly specified and defined, the terms "mounted," "interconnected," "connected," "fixed" and the like are used broadly, and may be, for example, fixed connections, detachable connections, or integral connections; may also be mechanical or electrical connections or intercommunication; may also be direct connections or indirect connections via intervening structures; may also be inner communications or interactions of two elements, which can be understood by those skilled in the art according to specific situations, unless otherwise explicitly specified.

In the present disclosure, unless otherwise explicitly specified and defined, a structure in which a first feature is "on" or "below" a second feature may include an implementation in which the first feature is in direct contact with the second feature, and may also include an implementation in which the first feature and the second feature are not in direct contact with each other, but are contacted via an additional feature formed therebetween. Furthermore, a first feature "on," "above," or "on top of" a second feature may include an implementation in which the first feature is right or obliquely "on," "above," or "on top of" the second feature, or just means that the first feature is at a height higher than that of the second feature; while a first feature "below," "under," or "on bottom of" a second feature may include an implementation in which the first feature is right or obliquely "below," "under," or "on bottom of" the second feature, or just means that the first feature is at a height lower than that of the second feature.

Although the implementations of the present disclosure have been shown and described above, it can be understood that the above implementations are exemplary and shall not be understood as limitation to the present disclosure, and changes, modifications, alternatives and variations can be made in the above implementations within the scope of the present disclosure by those skilled in the art.

What is claimed is:

1. An earphone, comprising:
   an ear hook portion provided with a first magnetic attraction member;
   an earphone portion provided with a second magnetic attraction member, the second magnetic attraction member attracting and cooperating with the first magnetic attraction member such that the earphone portion is connected with the ear hook portion; and
   a heart rate detection module arranged on at least one of the ear hook portion or the earphone portion, wherein the earphone portion is provided with an earphone chip, the heart rate detection module is electrically connected to the earphone chip, the earphone further comprises a connection sensor for detecting a connection state between the ear hook portion and the earphone portion, and the connection sensor is electrically connected to the earphone chip.

2. The earphone according to claim 1, wherein an end of the ear hook portion is defined with a first limit groove, the first magnetic attraction member is arranged in the first limit groove, an end of the earphone portion is defined with a second limit groove, and the second magnetic attraction member is arranged in the second limit groove.

3. The earphone according to claim 1, wherein at least one of the first magnetic attraction member or the second magnetic attraction member is a magnet.

4. The earphone according to claim 1, wherein the first magnetic attraction member is a magnet, the connection sensor is a Hall sensor arranged on the earphone portion, and the Hall sensor is spaced apart from the second magnetic attraction member when the second magnetic attraction member is a magnet.

5. The earphone according to claim 1, wherein the earphone portion is further provided with a Bluetooth module electrically connected to the earphone chip.

6. The earphone according to claim 1, wherein the heart rate detection module is arranged on the earphone portion, and the earphone portion is provided with a first battery electrically connected to the heart rate detection module.

7. The earphone according to claim 1, wherein the heart rate detection module is arranged on the ear hook portion, and the ear hook portion is provided with a second battery electrically connected to the heart rate detection module.

8. The earphone according to claim 7, wherein one of the ear hook portion and the earphone portion is provided with an elastic piece, the other one of the ear hook portion and the earphone portion is provided with a contact point, and the heart rate detection module is electrically connected to the earphone chip through a cooperation between the elastic piece and the contact point.

9. The earphone according to claim 7, wherein one of the ear hook portion and the earphone portion is provided with a pin, the other one of the ear hook portion and the earphone portion is provided with a jack, and the heart rate detection module is electrically connected to the earphone chip through a cooperation between the pin and the jack.

10. The earphone according to claim 1, wherein the ear hook portion and the earphone portion are detached and placed separately in a charging box when the earphone portion is being charged in the charging box.

11. The earphone according to claim 1, wherein the ear hook portion and the earphone portion are detachably connected through the first magnetic attraction member and the second magnetic attraction member such that a user can wear the earphone portion with or without the ear hook portion.

12. The earphone according to claim 1, further comprising:
   in response to detecting the connection state between the ear hook portion and the earphone portion, sending, by the connection sensor, a signal indicative of a user about to enter a sport mode.

13. The earphone according to claim 12, further comprising:
   in response to receiving the signal indicative of the user about to enter the sport mode, controlling, by the earphone chip, the heart rate detection module to collect heart rate of the user.

14. The earphone according to claim 12, further comprising:
   in response to receiving the signal indicative of the user about to enter the sport mode, switching a play mode of the earphone to a sport style.

15. The earphone according to claim 14, wherein the sport style comprises a preset equalizer mode, or the sport style is set to play a preset track with a strong rhythm.

16. The earphone according to claim 1, further comprising:
   in response to detecting a disconnection state between the ear hook portion and the earphone portion, controlling the heart rate detection module to stop collecting heart rate.

17. The earphone according to claim 1, further comprising:
   in response to detecting a disconnection state between the ear hook portion and the earphone portion, switching a play mode of the earphone to a normal style.

18. The earphone according to claim 1, further comprising:
   in response to detecting the connection state or a disconnection state between the ear hook portion and the earphone portion, automatically turning on or off the heart rate detection module or switching a music playing mode.

19. The earphone according to claim 2, wherein the first magnetic attraction member is in an interference fit with the first limit groove, or the second magnetic attraction member is in an interference fit with the second limit groove.

* * * * *